United States Patent [19]

Bonnell

[11] Patent Number: 5,050,586

[45] Date of Patent: Sep. 24, 1991

[54] MANDIBLE MANIPULATOR

[75] Inventor: Leonard Bonnell, Huntingdon Valley, Pa.

[73] Assignee: Leonard Medical, Huntingdon Valley, Pa.

[21] Appl. No.: 410,286

[22] Filed: Sep. 21, 1989

[51] Int. Cl.⁵ ............................................. A61B 1/24
[52] U.S. Cl. ....................................... 128/12; 128/15; 128/20; 433/42
[58] Field of Search ........................ 128/12, 13, 15, 16, 128/20; 433/41, 42, 214

[56] References Cited

U.S. PATENT DOCUMENTS

| | | | |
|---|---|---|---|
| 853,031 | 5/1907 | Prentis | 128/12 X |
| 1,137,585 | 4/1915 | Craig, Jr. | 128/346 |
| 1,388,421 | 8/1921 | Forgrave | 128/12 |
| 1,805,309 | 5/1931 | Eggler | 128/346 |
| 2,382,385 | 8/1945 | Condit | 128/346 |
| 2,505,056 | 4/1950 | Messine | 128/12 |
| 2,703,452 | 3/1955 | Getz | 433/42 X |
| 2,969,059 | 1/1961 | Meek et al. | 128/12 |
| 3,132,647 | 5/1964 | Corniello | 128/346 |
| 3,510,923 | 5/1970 | Blake | 128/346 |
| 4,169,478 | 10/1979 | Hickmann | 128/346 |
| 4,466,437 | 8/1984 | Dyck et al. | 128/346 X |
| 4,526,172 | 7/1985 | Stephenson | 128/346 X |
| 4,602,905 | 7/1986 | O'Keefe | 433/41 |

OTHER PUBLICATIONS

Arthropedics, "New Horizons in TMJ Arthroscopy", Brochure, 1987.

Primary Examiner—William H. Grieb

[57] ABSTRACT

An apparatus for the manipulation of the mandible comprising, in one embodiment, a handle, a mouth tray for insertion into said patient's mouth and a chin rest for positioning under said patient's chin. The distance between the chin rest and the mouth tray is adjustable so as to hold the patient's mandible firmly between the chin rest and the mouth tray and permit the physician to manipulate the patient's mandible using only one hand.

10 Claims, 4 Drawing Sheets

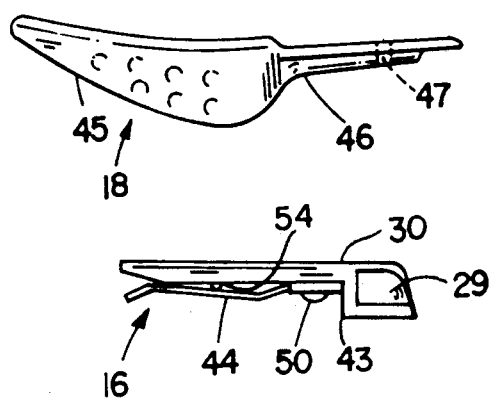
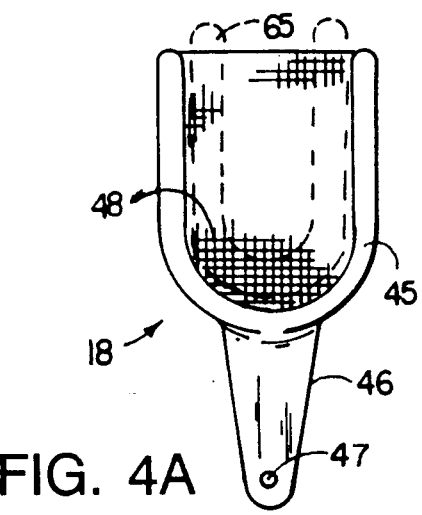
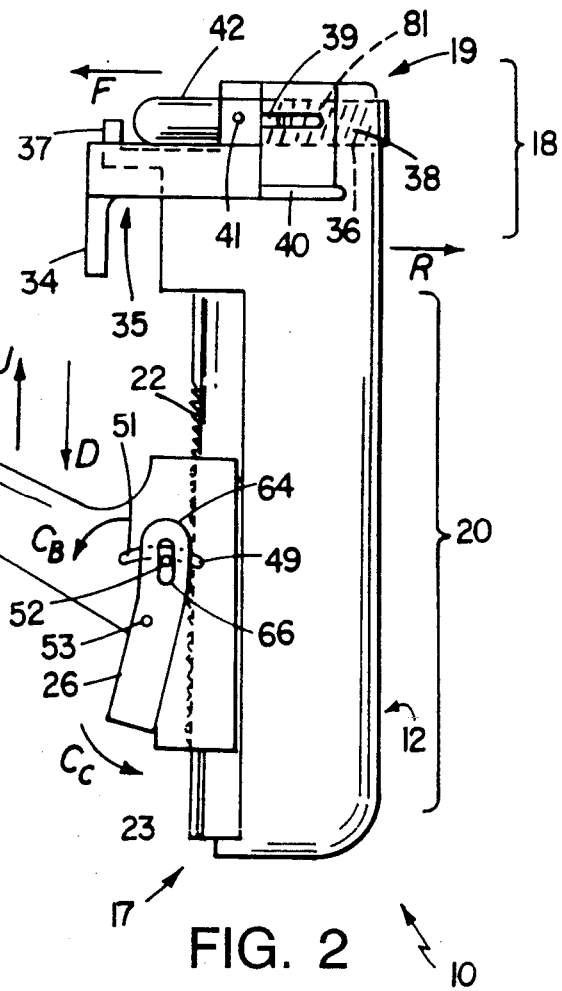
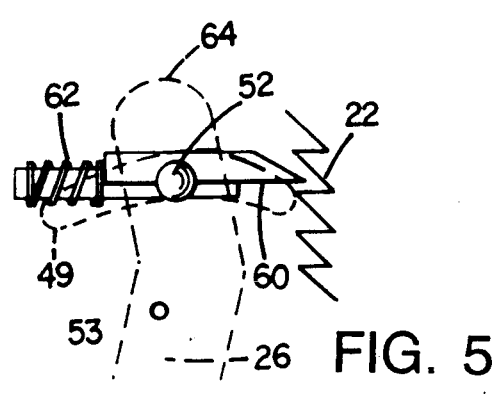

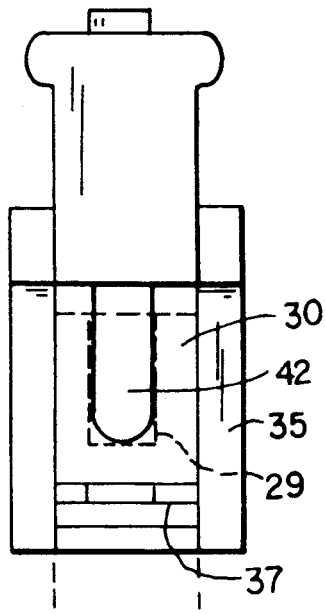
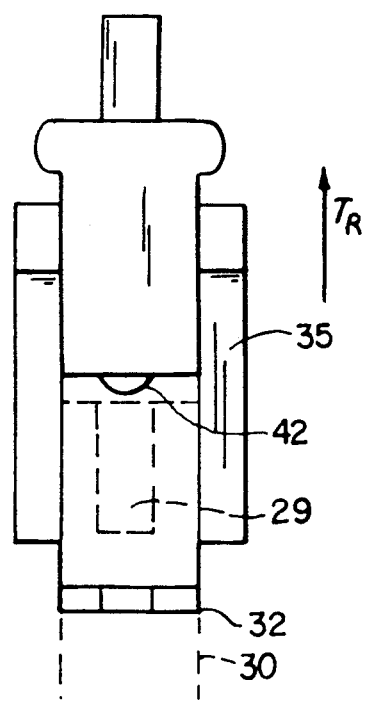
FIG. 6A  FIG. 6
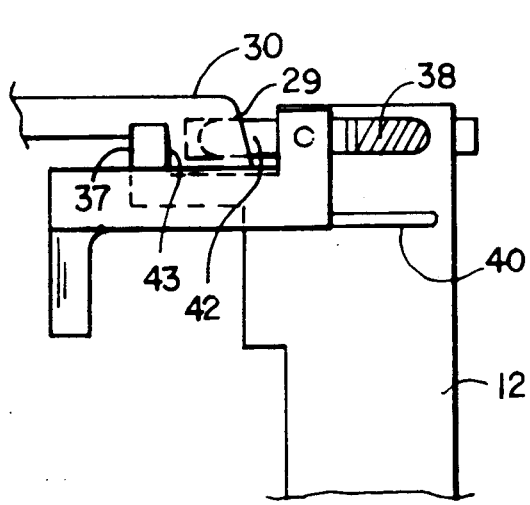
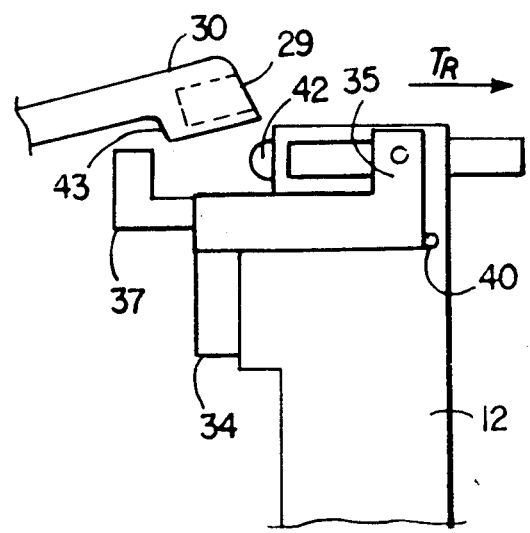
FIG. 7A  FIG. 7

MANDIBLE MANIPULATOR

BACKGROUND OF THE INVENTION

This invention relates to the field of instruments for positioning a portion of the body for a medical procedure.

The flexibility of the human jaw is due to the structure of the temporomandibular joints (TMJ). The condyles of the mandible meet with the temporal regions of the skull to form what are strictly speaking the temporomandibular articulations. Each articulation actually is formed from two joints The first joint occurs between a condyle and interarticular fibro-cartilage. The second joint occurs between the fibro-cartilage and the glenoid cavity of a temporal region of the skull. This double joint arrangement allows the jaw extensive movement.

The temporomandibular joints are susceptible to a variety of disease states and injuries. Many of these problems are correctable by surgical intervention; however, before performing surgery on the temporomandibular joint, it is desirable for the surgeon to view the joint. By visualizing the TMJ, the physician can determine if surgical intervention is indicated. Typically the temporomandibular joint is visualized arthoscopically using an endoscope with a video camera. In order to visualize the TMJ, the jaw must be manipulated, that is, for example, drawn downward and forward to create a space in the capsule of the temporomandibular joint to allow an endoscope or other instruments to be presented into the capsule.

To manipulate the jaw, the physician or assistant in one technique wraps his sterile gloved thumb with a sterile gauze and inserts his thumb in the patient's mouth to grip the patient's jaw between his thumb and fingers. This technique, however, exposes the thumb to the patient's teeth, thereby creating the risk of infection for the person manipulating the jaw. Additionally, since the thumb is of a finite thickness, the manipulation is unable to include the complete closing of the jaw and thereby precludes moving the jaw through the dynamic range of which the jaw is capable.

A second technique requires the gripping of the jaw with a towel clip. A towel clip is an instrument which resembles miniature ice tongs. The pincers of the tongs penetrate the skin and muscle of the patient's jaw, and the physician can then, by pulling on the handle, move the jaw as he wishes. In addition to the inherent pain, this procedure leaves the patient with two puncture holes.

The present invention provides an apparatus by which the surgeon, using only one hand, may manipulate the jaw of the patient into the correct position for arthoscopic examination of the full range of jaw motion without exposing the surgeon to infection and without injuring the patient.

SUMMARY OF THE INVENTION

According to one aspect of the invention, an apparatus for the manipulation of the mandible comprises a handle, a mouth tray for insertion into said patient's mouth and a chin rest for positioning under said patient's chin. The mouth tray is removably attached to the handle. The chin rest is movably attached to the handle such that the distance between the chin rest and the mouth tray is adjustable so as to hold the patient's mandible firmly between the chin rest and the mouth tray. With such an apparatus, the physician can manipulate the patient's mandible using only one hand.

Embodiments of the invention may have any or all of the following features. The mouth tray is removably attached. The mouth tray has a generally semicircular portion of a size and shape so as to generally approximate the lower jaw of the patient, a stem portion extending from the generally semicircular portion and an attachment surface made of a gauze-like material to hold dental impression material. The chin rest has an instrument attachment portion, movably mounted upon the instrument body; an arm extending generally from the instrument attachment portion; and a rest surface, mounted at the end of the arm, for contact beneath the patient's chin. The instrument attachment portion has an enclosure body; an engagement tooth slidably mounted within the enclosure to permit movement of the engagement tooth toward and away from the instrument body; a trigger having a top and bottom portion and rotatably mounted on the enclosure body by a pivot between the top and bottom portions of the trigger; a connecting means connecting the top portion of the trigger and the engagement tooth; and a tooth biasing spring, located within the enclosure for biasing the spring toward the instrument body. The instrument body further has a rack such that the engagement tooth is adapted for movement between a first position engaged with the rack and a second position removed from engagement with the rack. The instrument body also has a front part and a rear part and a mouth tray attachment portion, which has a stop, a groove defined by the instrument body and extending from the front part to the rear part of the instrument body, a carriage slidably mounted in the groove, a piston in communication with the carriage and slidably mounted in a piston hole extending from the front part to the rear part of the instrument body, and a piston biasing spring mounted in the piston hole and in communication with the piston to normally bias the piston toward the stop. The mouth tray further has a gripper having a mouth tray holding portion and a piston engagement portion for attaching the mouth tray to the mouth tray attachment portion.

Another aspect of the invention is a method for manipulating the mandible of a patient having the steps of providing a medical apparatus as described above, placing the mouth tray into the mouth of said patient adjusting the relative positions of the mouth tray and chin rest along the instrument body in a manner to hold the patient's mandible firmly between the chin rest and the mouth tray; and moving the instrument body to position the patient's mandible as desired.

BRIEF DESCRIPTION OF THE DRAWINGS

FIG. 2 is a side view of the handle portion of the apparatus of FIG. 1;

FIG. 3 is a side view of the tray gripper portion of the apparatus;

FIG. 4 is a side view of the mouth tray portion of the apparatus;

FIG. 4A is a top plan view of the mouth tray portion of FIG. 4;

FIG. 5 is an enlarged, somewhat diagrammatic side view of the chin portion release of the apparatus of FIG. 2;

FIG. 6 is a top plain view of the apparatus of FIG. 1, with the mouth tray gripper piston pin retracted;

FIG. 6A is a similar view with the mouth tray gripper piston released;

FIG. 7 is a side elevation of the apparatus of FIG. 1 with the mouth tray gripper piston retracted so as to allow the mouth tray gripper to be mounted in the handle, while FIG. 7A is a similar view of the apparatus with the mouth tray gripper piston released to hold the mouth tray gripper in position in the handle.

DESCRIPTION OF THE PREFERRED EMBODIMENT

Figure 1:
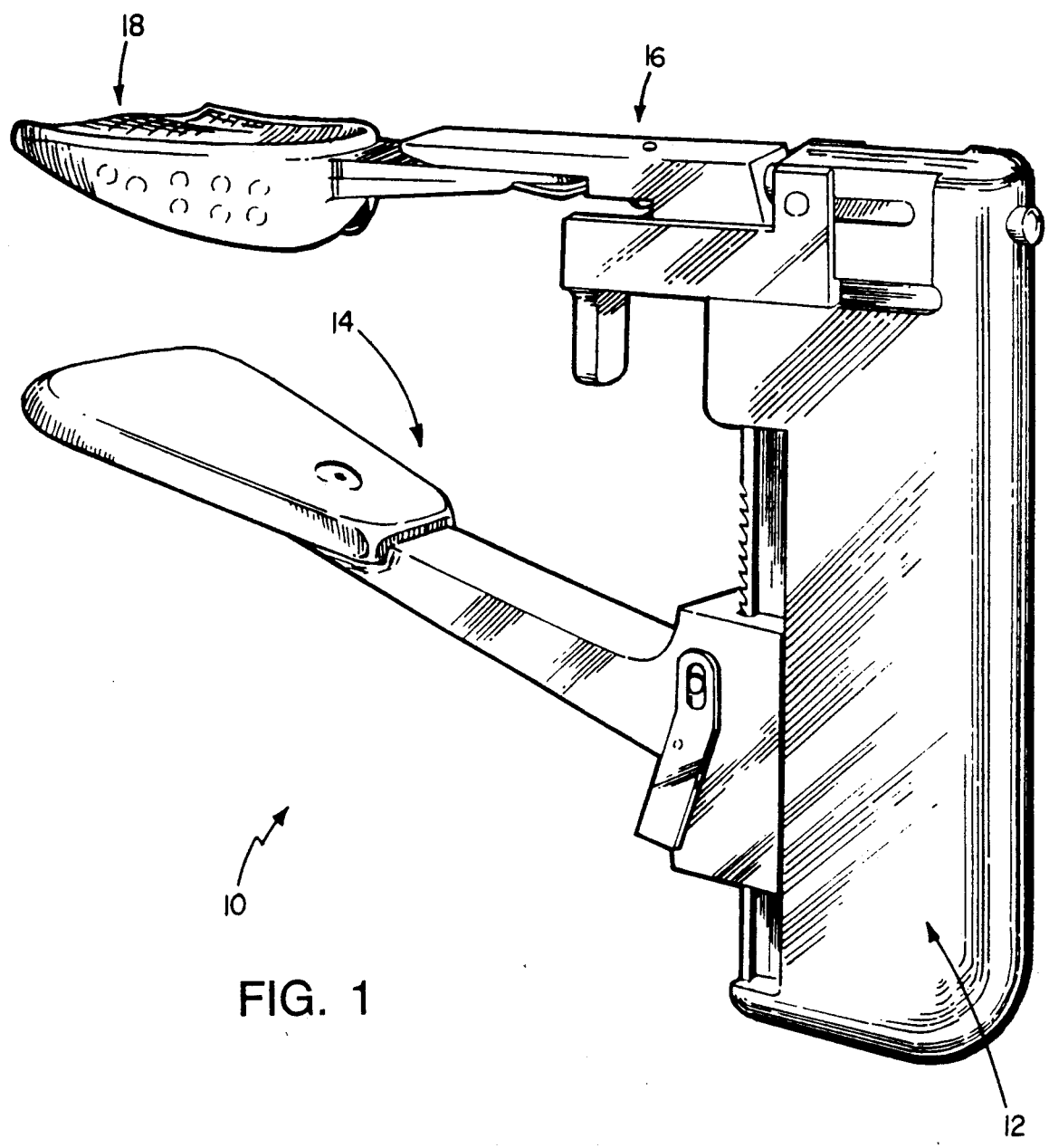
FIG. 1 is a perspective view of a mandible manipulation apparatus of the invention.

Referring to FIG. 1, a mandible manipulator 10 of the invention includes body 12, a chin rest section 14, a mouth tray gripper 16 and a separable mouth tray 18. The instrument proper, consisting of body, chin rest section and mouth tray gripper are steam autoclavable for reuse; the mouth tray is disposable, preferably for one-time and at least one patient use.

Referring also to FIG. 2, the body 12 comprises a handle 20, having a forward portion 17 upon which is mounted a rack 22, and an upper portion 18 which provides structure 19 for attachment of the mouth tray gripper 16. The body 12 is typically constructed from a strong, light-weight plastic, e.g. Delrin ™, capable of withstanding the temperatures reached in a steam autoclave (about 135°-275° C.).

The mouth tray gripper attachment structure 19 comprises a carriage 35 which is slidably mounted in a groove 40 in upper portion 18 of the body 12. The carriage 35 is anchored by an attachment pin 41 to a mouth tray gripper piston 42 which is slidably located in a horizontal bore 36 in the upper portion 18 of the body 12. The attachment pin 41 communicates with the mouth tray gripper piston 42 through a slot 39 in the handle 20. A spring 38 located in horizontal bore 36 engages rear surface 81 of the mouth tray gripper piston 42 to bias the mouth tray gripper piston 42 and the carriage 35 forward, as shown by arrow F. The front portion of the carriage 35 includes a carriage trigger 34, oriented at right angles to the carriage 35. The upper portion of the body 12 defines a stop 37. The carriage 35, rack 22 and mouth tray gripper piston 34 are constructed of aluminum, or other suitable material.

Referring also to FIG. 3, the mouth tray gripper 16 has a rigid body 30, the rearward end of which is drilled to form a gripper piston hole 29 sized to receive the mouth tray gripper piston 42. The mouth tray gripper 16 also has a seating portion 43 and a flat spring 44 made, for example, of stainless steel, attached to the rigid body 30 by a screw 50. A mouth tray pin 54, between the flat spring 44 and the rigid body 30, engages the mouth tray !8, as shall be described. The mouth tray gripper 16 is also constructed of aluminum or other suitable autoclavable material, and is removably attached to the instrument body 12 by the mouth tray gripper piston 42 and stop 37 by engaging the seating portion 43 to rest against the stop 37 and engaging the mouth tray gripper piston 42 in the gripper piston hole 29 thereby holding the mouth tray gripper 16 mounted upon the upper portion 18 of the instrument body 12.

Referring also to FIG. 4, the mouth tray section 18 includes a mouth tray 45 with a mouth tray stem 46. The tray stem 46 has a retaining hole 47 located generally perpendicularly to the plane of the mouth tray 45 such that when the mouth tray 18 is removably attached to the mouth tray gripper !6, the mouth tray stem 46 is held between the flat spring 44 and the rigid body 30, with the mouth tray pin 54 engaged in the retaining hole 47.

Referring now to FIG. 4A, the mouth tray 45 itself is generally semicircular in shape so as to fit within the patient's mouth and approximate the shape of the patient's lower jaw. The mouth tray stem 46 attaches to the mouth tray 45 at approximately the center of the semicircle. A cheese cloth or gauze-like material 48 forms a generally planar surface within the confines of the mouth tray semicircle. The mouth tray portion 18 is made of an FDA approved plastic such as polyethylene and is disposable.

The chin rest section 14 has a generally triangular chin rest 28 attached to an extension arm 24 which is movably attached to the rack 22 by the release enclosure 23. A chin rest trigger 26 is rotatably mounted by a pivot pin 53 to the release enclosure 23. The upper portion 64 of the chin rest trigger 26 rotates counterclockwise (arrow $C_B$) about the pivot 53 when the chin rest trigger 26 is depressed counter clockwise (arrow $C_C$). The upper portion of the chin rest trigger 26 comprises a slot in which a retracting pin 52 is slidably mounted. The chin rest 28 and extension arm 24 may also be constructed of the same material forming the body 12. The chin rest trigger 26 may be constructed of aluminum Referring also to FIG. 5 the retracting pin 52 passes through a generally curved slot 49 in the release enclosure 23, and attaches to engagement tooth 60. The engagement tooth 60 is slidably mounted within the release enclosure 23 and biased by a spring 62 toward the rack 22. In the normally biased condition, the engagement tooth 60 is held in engagement by the ramp surfaces of the rack 22 teeth. The combination of the biasing spring 62, the shape of the engagement tooth 60 (such that one surface is at 0° to the direction of bias while the other surface is at a ramp angle less than 90°) and the shape of the rack 20 teeth (such that one surface is at 0° to the direction of spring bias while the other surface is at a ramp angle between 180° and 270°) allows the release enclosure 23 to be moved rapidly in the upward direction by a simple application of force in that direction (arrow U). The opposed angular surfaces of the rack 22 teeth and the engagement tooth 60 slide over each other as the release enclosure 23 is moved upward. Ratcheting movement is prevented in the reverse direction (downward) by the engagement of the opposed generally horizontal surface of the engagement tooth 60 and the generally horizontal surfaces of the rack 22 teeth.

When the chin rest trigger 26 is depressed, the upper portion of the trigger 64 rotates counter clockwise (arrow $C_B$) about the pivot pin 53 to cause the retracting pin 52 to move forward (arrow F) within slot 49, pulling the engagement tooth 60 forward and away from the rack 22, compressing spring 62. Once the engagement tooth 60 is pulled away from the rack 22, the release enclosure 23 can slide up and down (arrow D) along the rack 22. When the chin rest trigger 26 is released, the spring 62 once again biases the engagement tooth 60 toward the rack 22 causing the retracting pin 52 to move toward the rack 22 along the slot 49 and causing the upper portion 64 of the chin rest trigger 26 to move clockwise about the pivot 53.

When the mouth tray is in use, a dental impression material (shown in phantom 65, FIG. 4A) such as Permagum TM is pressed onto the gauze-like material 48 along the circumference of the mouth tray 45. The impression material becomes embedded in the gauze like material. When the tray is placed in the patient's mouth, the dental impression material takes an impression of the teeth of the patient's lower jaw and thereby, when hardened, forms a strong but removable attachment with the patient's lower teeth.

Figure 8:
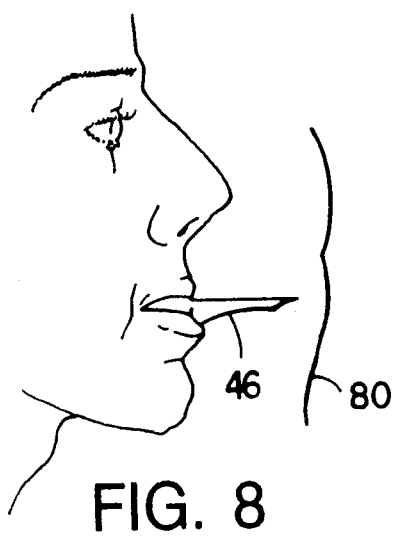
FIGS. 8, 9 and 10 are sequential somewhat diagrammatic views depicting use of the apparatus of the invention on a patient in preparation for undergoing mandibular manipulation.

The manipulation procedure begins with sterile mixing of the components of the dental impression material together until they have a malleable consistency. This malleable material is formed into a roughly cylindrical shape and pressed into the gauze around the circumference of the mouth tray 45 (FIG. 4A). Referring to FIG. 8, the mouth tray 45 is placed in the patent's mouth with the mouth tray stem 46 protruding from the patient's mouth, and the patient's jaw is closed and the dental impression material allowed to harden. (This step may take place well before the manipulation procedure, and when the impression material has hardened, the mouth tray 45 can be removed from the patient's mouth for later use.)

Figure 9:
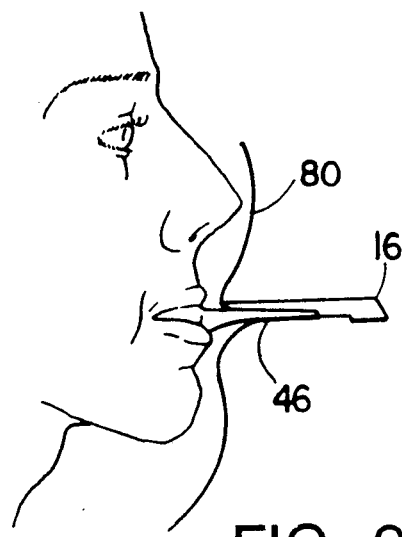

Once the impression material has hardened, a sterile drape 80 of thin material is placed over the patient's face and tray stem 46. The mouth tray gripper 16 is then placed so as to engage the tray stem 46 (through the drape, without puncturing the drape, so as to maintain sterility) between the rigid body 30 and the flat spring 44 such that the mouth tray pin 54 engages the pin retaining hole 47 (FIG. 9).

The mouth tray gripper 16 is next attached to the sterilized body 12 and chin rest 14 portions of the manipulator 10. The trigger 26 is squeezed and the chin rest 14 is moved down into its lowest position on the body 12. The handle 20 is gripped in the physician's hand, with the physician's forefinger positioned on the carriage trigger 34. Referring also to FIGS. 6 and 7, the carriage trigger 34 is depressed (arrow $T_R$) causing the carriage 35 and the mouth tray gripper piston 42 to retract along the groove 40 away from the stop 37 compressing spring 43 (FIGS. 6 and 7). The body 12 is then positioned to engage the mouth tray gripper 16 (shown in phantom in FIG. 6) by placing the seating portion 43 of the mouth tray gripper body 30 against the stop 37.

Referring to FIGS. 6A and 7A, once the mouth tray seating portion 43 is in position between the stop 37 and the mouth tray gripper piston 42, the carriage trigger 34 is released and the mouth tray gripper piston 42 is moved forward by spring 38 toward the stop 37, engaging the mouth tray gripper piston 42 in the gripper piston hole 29 and locking the mouth tray gripper seating portion 43 between the stop 37 and the gripper piston 42.

Figure 10:
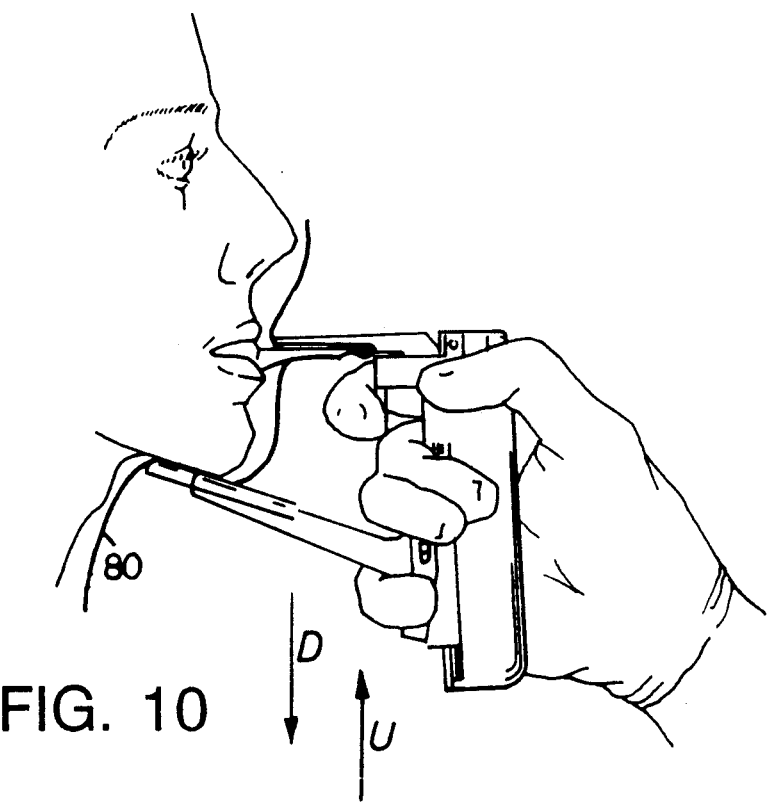

Once the mouth tray gripper 16 is secured to the handle 12, the chin rest 28, shielded by the drape 80, is moved upwardly along the rack 22, until it is brought into contact with the patient's chin FIG. 10 (either by ratchet or by gripping the trigger 26 for quiet sliding motion). The chin rest 28 is then moved upward toward the patient's chin another 2 or 3 notches along the rack 22 to form a tight grip on the patient's jaw. The physician can then, using only one hand, manipulate the jaw as desired.

To remove the manipulator 10 from the patient, the chin rest trigger 26 is depressed, e.g. using the lower fingers of the same hand that is doing the manipulation, causing the retracting pin 52 to move rearwardly in the generally curvalinear slot 49 in the release enclosure 23. This in turn causes the engagement tooth 60 to slide forwardly within the release enclosure 23, disengaging the engagement tooth 60 from the rack 22 and allowing the chin rest 28 to be moved downwardly (arrow D) along the handle 12 away from the patient.

The carriage trigger 34 is then depressed again using the forefinger of the hand holding the manipulator, causing the gripper piston 42 to move away from the mouth tray gripper 16, disengaging it from the gripper piston hole 29. The handle 12 can then be rotated clockwise about the junction of the stop 37 and the seating position 42 of the tray gripper 16, separating the handle 12 from the mouth tray gripper 16.

The thin spring 44 of the mouth tray gripper 16 is then moved away from the rigid body 30 to release the mouth tray stem 46. The mouth tray 18 can then be removed from the patient's mouth.

One skilled in the art will realize that other embodiments are with the scope and spirit of the embodiment and as such the invention is limited only by the claims.

What is claimed is:

1. A medical apparatus for the manipulation of the mandible comprising:

an instrument body defining a handle;

a mouth tray of a size suitable for insertion into a patient's mouth and having a member of a shape generally approximating that of the lower jaw of a patient, said mouth tray adapted for attachment to said instrument body;

a chin rest defining a surface adapted for engagement beneath a patient'chin, said chin rest attached to said instrument body; and means for adjustment of the relative positions of said mouth tray and said chin rest along said instrument body in a manner to hold the patient's mandible firmly between said chin rest and the said mouth tray.

2. The apparatus of claim 1 wherein instrument body comprises means for removable attachment of said mouth tray.

3. The apparatus of claim 1 wherein said chin rest comprises:

an instrument attachment portion, movably mounted upon said instrument body;

an arm extending generally from said instrument attachment portion; and a rest portion defining said surface for contact beneath said patient's chin, said rest portion mounted at the end of said arm.

4. The apparatus of claim 1 wherein said instrument body has a front part and a rear part and comprises a mouth tray attachment portion for attachment of said mouth tray to said instrument body, said mouth tray attachment portion comprising:

a stop;

a groove defined by said instrument body and extending from the front part toward the rear part of the instrument body;

a carriage slidably mounted in said groove;

a piston slidably mounted in a piston hole defined by said instrument body, said piston hole extending from said front part toward said rear part of said instrument body and in communication with said carriage; and a piston biasing spring mounted in said piston hole and in communication with said piston in a manner to normally bias said piston toward said stop.

5. The apparatus of claim 4 wherein said mouth tray further comprises a gripper for attachment of said mouth tray to said mouth tray attachment portion of said instrument body, said gripper comprising:
 a mouth tray holding portion; and
 a piston engagement portion.

6. A medical apparatus for the manipulation of the mandible comprising:
 an instrument body defining a handle;
 a mouth tray of a size suitable for insertion into a patient's mouth and having a member of a shape generally approximating that of the lower jaw of a patient, said mouth tray adapted for attachment to said instrument body;
 a chin rest defining a surface adapted for engagement beneath a patient's chin, said chin rest attached to said instrument body; and
 means for adjustment of the relative positions of said mouth tray and said chin rest along said instrument body in a manner to hold the patient's mandible firmly between said chin rest and the said mouth tray, wherein said mouth tray further comprises:
 a stem portion extending from the member of the shape generally approximating that of the lower jaw of the patient; and
 an attachment surface for dental impression material extending generally in a plane within the member of the shape generally approximating that of the lower jaw of the patient.

7. The apparatus of claim 6 wherein said attachment surface comprises gauze-like material.

8. A medical apparatus for the manipulation of the mandible comprising:
 A. an instrument body defining a handle;
 B. a mouth tray of a size suitable for insertion into a patient's mouth and having a member of a shape generally approximating that of the lower jaw of a patient, said mouth tray adapted for attachment to said instrument body;
 C. a chin rest defining a surface adapted for engagement beneath a patient's chin, said chin rest comprising:
  i. an instrument attachment portion movably mounted upon said instrument body,
  ii. an arm extending generally from said instrument attachment portion; and
  iii. a rest portion defining said surface for contact beneath said patient's chin, said rest portion mounted at the end of said arm; and
 D. means for adjustment of the relative positions of said mouth tray and said chin rest along said instrument body in a manner to hold the patient's mandible firmly between said chin rest and the said mouth tray,
wherein said instrument attachment portion comprises
 i. an enclosure body defining an enclosure;
 ii. an engagement tooth slidably mounted within said enclosure, in a manner to permit movement of the engagement tooth toward and away from said instrument body;
 iii. a trigger, said trigger having a top and bottom portion, said trigger rotatably mounted on said enclosure body by a pivot engaging said trigger between said top and bottom portions, such that as the bottom portion rotates clockwise, the top portion also rotates clockwise;
 iv. means for connecting said top portion of said trigger and said engagement tooth; and
 v. a tooth biasing spring, located within said enclosure for biasing said spring toward said handle.

9. The apparatus of claim 8 wherein said instrument body further comprises a rack, and said engagement tooth is adapted for movement between a first position engaged with said rack and a second position removed from engagement with said rack.

10. A method for manipulating the mandible of a patient comprising the steps of:
 providing a medical apparatus comprising an instrument body defining a handle; a mouth tray of a size suitable for insertion into a patient's mouth and having a member of a shape generally approximating that of the lower jaw of a patient, said mouth tray attached to said instrument body; a chin rest defining a surface adapted for engagement beneath a patient's chin, said chin rest attached to said instrument body; and means for adjustment of the relative positions of said mouth tray and said chin rest along said instrument body in a manner to hold the patient's mandible firmly between said chin rest and said mouth tray;
 placing said mouth tray into the mouth of said patient;
 adjusting the relative positions of said mouth tray and chin rest along said instrument body in a manner to hold the patient's mandible firmly between said chin rest and said mouth tray; and
 moving said instrument body to position the patient's mandible as desired.

* * * * *

UNITED STATES PATENT AND TRADEMARK OFFICE
CERTIFICATE OF CORRECTION

PATENT NO. : 5,050,586

DATED : 09/24/91

INVENTOR(S) : Leonard Bonnell

It is certified that error appears in the above-identified patent and that said Letters Patent is hereby corrected as shown below:

Col. 4, line 2, "!6", should be --16--.

Signed and Sealed this

Ninth Day of March, 1993

Attest:

STEPHEN G. KUNIN

*Attesting Officer*     *Acting Commissioner of Patents and Trademarks*